United States Patent [19]

Kawahara et al.

[11] Patent Number: 5,304,127
[45] Date of Patent: Apr. 19, 1994

[54] INFUSION APPARATUS ABLE TO RECOGNIZE AN APPROPRIATE TIME FOR SERVICING

[75] Inventors: Masafumi Kawahara, Nara, Japan; Joseph B. Matthews, Grayslake; Thomas Callaghan, Algonquin, both of Ill.

[73] Assignees: Sharp Kabushiki Kaisha, Osaka, Japan; Baxter International Incorporated, Deerfield, Ill.

[21] Appl. No.: 42,014

[22] Filed: Apr. 2, 1993

[30] Foreign Application Priority Data

Apr. 3, 1992 [JP] Japan .................. 4-081956

[51] Int. Cl.$^5$ ................ A61M 31/00; A61M 1/00
[52] U.S. Cl. .................... 604/65; 604/153; 128/DIG. 13
[58] Field of Search ............... 604/65-67, 604/151-155; 128/DIG. 12, DIG. 13

[56] References Cited

U.S. PATENT DOCUMENTS

| | | | |
|---|---|---|---|
| 4,191,184 | 3/1980 | Carlisle | 604/246 X |
| 4,308,866 | 1/1982 | Jelliffe et al. | 604/67 X |
| 4,469,481 | 9/1984 | Kobayashi | 604/67 |
| 4,845,487 | 7/1989 | Frantz et al. | 340/679 |
| 5,116,203 | 5/1992 | Natwick et al. | 417/53 |
| 5,131,816 | 7/1992 | Brown et al. | 417/2 |
| 5,207,642 | 5/1993 | Orkin et al. | 604/65 |

FOREIGN PATENT DOCUMENTS

53-18335  2/1978  Japan ..
3-216741  9/1991  Japan .

*Primary Examiner*—John D. Yasko
*Assistant Examiner*—Adam J. Cermak

[57] ABSTRACT

An infusion apparatus is provided with a clock, a power-on-time counter for counting a period of time in which power is supplied to the infusion apparatus from an AC power source or a backup battery for backing up the AC power source, a pump-on-time counter for counting a period of time in which a pump mechanism operates, and a battery-on-time counter for counting a period of time in which power is supplied to the infusion apparatus from the backup battery. A CPU displays a time value counted by the counters on a display unit. The time value displayed on the display unit indicates the degree of deterioration of charge capability of the backup battery, from which a time for replacing the backup battery and the other parts can be easily perceived.

4 Claims, 7 Drawing Sheets

INFUSION APPARATUS ABLE TO RECOGNIZE AN APPROPRIATE TIME FOR SERVICING

BACKGROUND OF THE INVENTION

1. Field of the Invention

The present invention relates to an infusion apparatus capable of informing its operator of the time for replacing the parts such as a battery of the apparatus.

2. Description of the Prior Art

Figure 5:
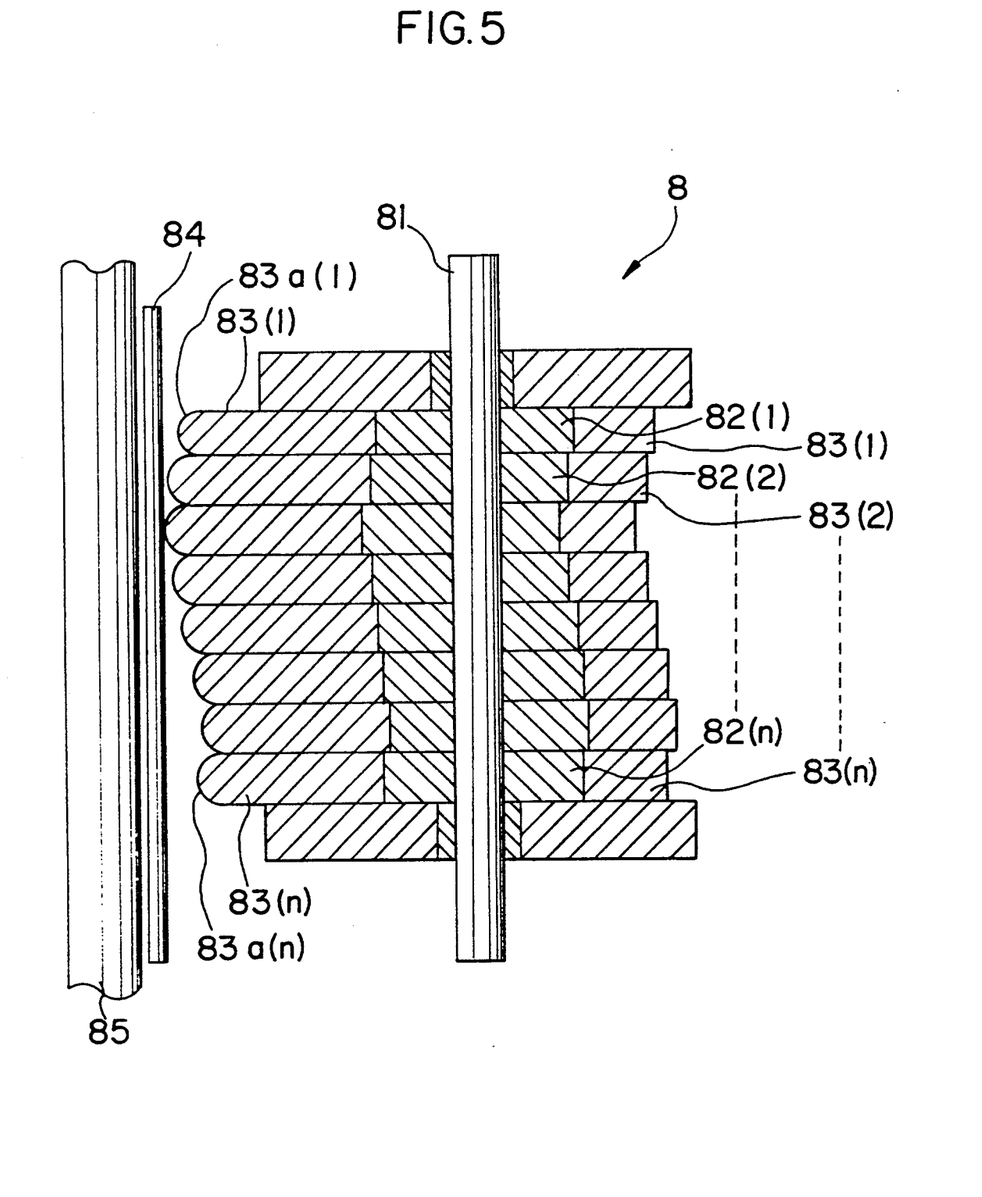
FIG. 5 is a view for explaining the pump mechanism of an ordinary infusion apparatus.

An infusion apparatus is used for infusing a medication fluid into a vein of a patient. There has been conventionally known in general an electromechanical positive pressure peristaltic type apparatus provided with a pump mechanism 8 as shown in FIG. 5. The pump mechanism 8 has a construction as follows. There are provided n number of fingers 83(1), 83(2), 83(n) driven by n number of cams 82(1), 82(2),..., 82(n) shifted in phase between every adjacent ones around a shaft 81 driven by a stepping motor (not shown). The fingers 83 are driven to move their ends 83a in a direction perpendicular to an administration tube 84. By peristaltically pressing the administration tube 84 downward against a door 85 with the fingers 83(1), 83(2), .., 83(n), a medication fluid supplied from an administration set (not shown) into the administration tube 84 is transferred.

Figure 6:
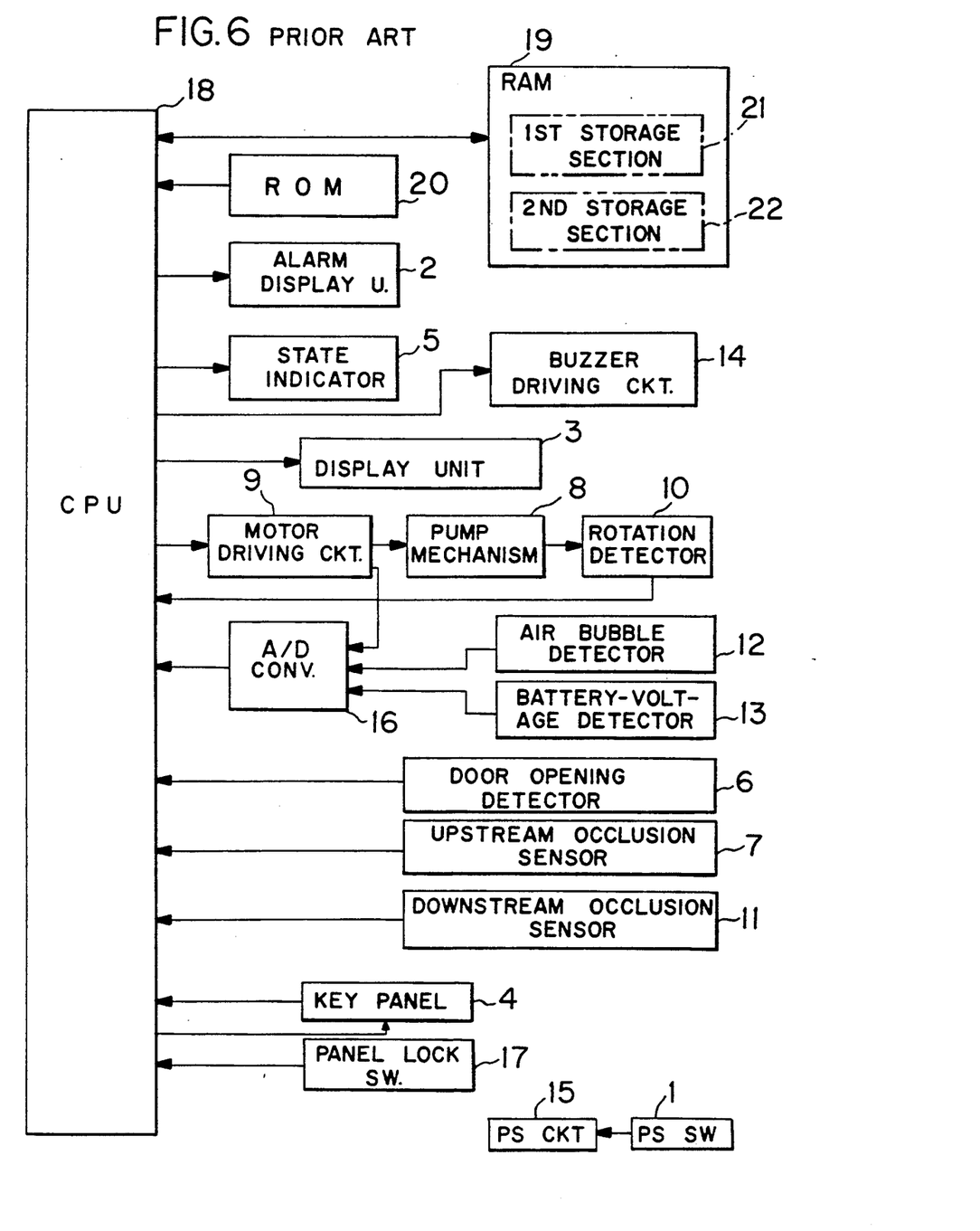
FIG. 6 is a block diagram of a conventional infusion apparatus.
Figure 7:
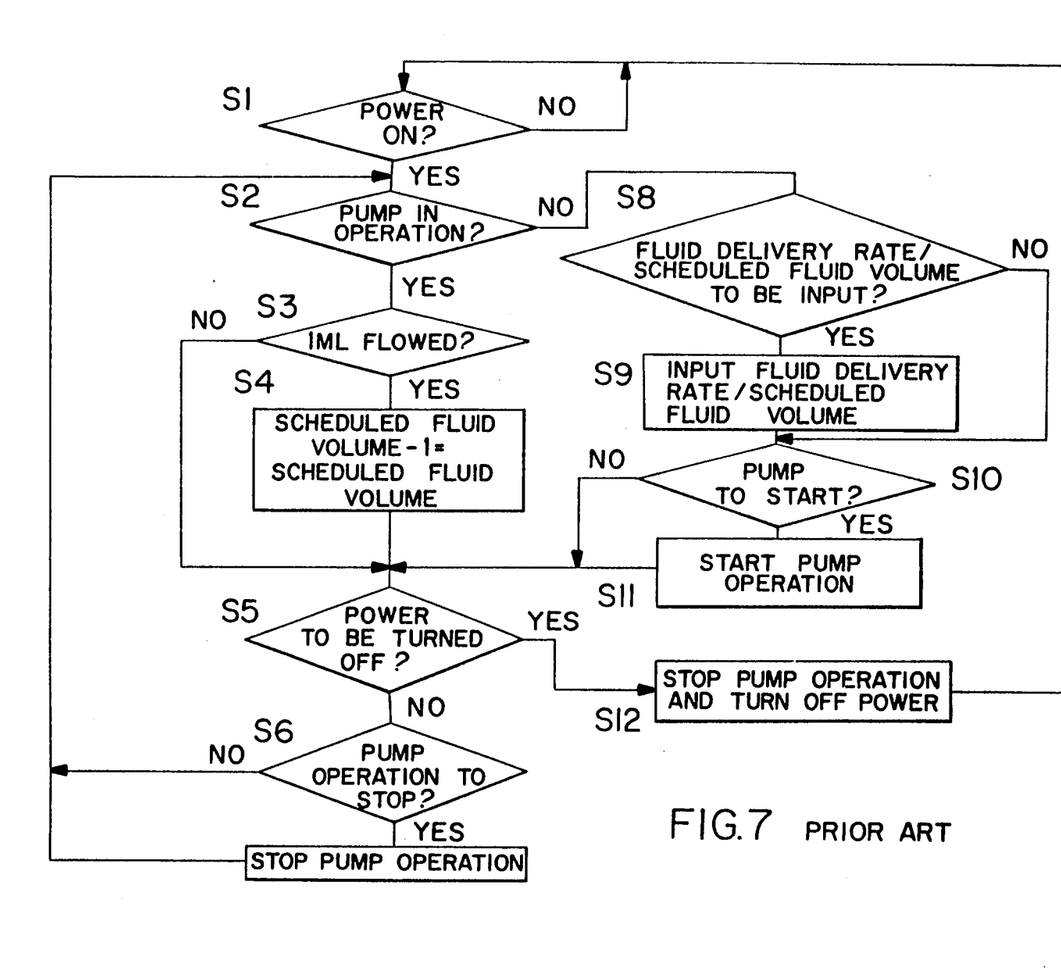
FIG. 7 is a flowchart of the operation of the conventional infusion apparatus.

FIG. 6 shows a block diagram of an infusion apparatus of the above-mentioned type, while FIG. 7 shows a flowchart of the operation of the infusion apparatus.

Referring to FIG. 6, a power supply switch, designated by numeral 1, turns on the power to the infusion apparatus when pressed. An alarm display unit, designated by numeral 2, displays 11 the alarm messages detected by the infusion apparatus. A display unit, designated by numeral 3, displays all the program data concerning fluid infusion such as fluid delivery rate, scheduled fluid volume, and accumulated fluid volume input to the infusion apparatus. A key panel, designated by numeral 4, has thereon numeral keys for inputting values of the fluid delivery rate and the scheduled fluid volume to set up values of operation spend and operation time for a pump mechanism 8, control keys for input assistance, a start key for starting the operation of the pump mechanism 8, a stop key for stopping the operation of the pump mechanism 8, and a call-up key for displaying the accumulated volume of fluid delivered and the like. An operation state indicator, designated by numeral 5, is a lamp that indicates which state the infusion apparatus is currently in among the states of alarm, fluid infusing operation, and operation stop. A lid opening detector, designated by numeral 6, detects whether or not the door 85 has come into the open position in order to set the administration tube 84 into the pump mechanism 8. The lid opening detector 6 is also necessary for stopping the operation of the pump mechanism 8 and generating an alarm when the door 85 is inadvertently opened while the pump mechanism 8 is in operation. An upstream occlusion sensor, designated by numeral 7, detects a pressure-reduction state due to the occurrence of any abnormality (e.g., clogged filter) in an administration set disposed between a medical solution container and the infusion apparatus, and is used to stop the operation of the pump mechanism 8 with generation of an alarm. The pump mechanism 8 includes a stepping motor. A motor driving circuit, designated by the numeral 9, drives the above-mentioned stepping motor according to a pulse output from a CPU 18. A pump mechanism rotation detector, designated by numeral 10, through the amount of rotation at the pump mechanism 8 detects that an incremental unit (e.g., 1 ml) of fluid has taken place, and then informs the CPU 18 of it. A downstream occlusion sensor, designated by numeral 11, detects a pressure-rise state within the administration tube between the infusion apparatus and the patient due to the occurrence of any abnormality such as occlusion, and is used to stop the operation of the pump mechanism 8 with generation of an alarm. An air bubble detector, designated by numeral 12, detects that air bubbles more than a prescribed amount have entered the administration tube. When this is detected, an alarm is generated while the operation of the pump mechanism 8 is stopped to thereby prevent the bubbles from entering into a patient's body. A battery-voltage detector, designated by numeral 13, detects any battery-voltage drop of a lead battery (not shown) used as a backup of an AC power supply. When this battery voltage drop is detected, the operation of the pump mechanism 8 is stopped while an alarm is generated. The lead battery is charged by a power supply circuit 15 when the infusion apparatus is in operation on the AC power line. A buzzer driving circuit, designated by numeral 14, generates a buzzer sound for informing doctors and nurses of the fact that the infusion apparatus has entered into the alarm state. A power supply circuit, designated by numeral 15, supplies power to all the circuits of the infusion apparatus. An analog-to-digital converter, designated by 16, converts the voltage resulting from a voltage conversion of a current supplied to the motor of the pump mechanism 8, the air bubble detector output level, the battery voltage level, and the like into digital values, and inputs them into the CPU 18. A panel lock switch, designated by numeral 17, serves to render the panel key and the power key input-inhibited so that the infusion apparatus will not be operated without permission by unauthorized personnel. A CPU (central processing unit), designated by numeral 18, controls the operation of the infusion apparatus. A RAM (memory section), designated by numeral 19, includes a first storage section for storing fluid delivery rate and scheduled fluid volume and a second storage section for storing various types of data used for arithmetic operation by the CPU 18. A ROM (read only memory; program section), designated by numeral 20, contains a program for operating the CPU 18.

The following describes the operation of the present infusion apparatus with reference to the flowchart shown in FIG. 7.

When the power to the infusion apparatus is turned on at step S1, it is determined at step S2 whether or not the pump mechanism 8 is in operation. When the pump mechanism 8 is not in operation, a request for inputting values of the fluid delivery rate and scheduled fluid volume takes place at step S8. Therefore, a doctor or nurse who intends to use the infusion apparatus inputs values of the fluid delivery rate and scheduled fluid volume at step S9 according to the desired medication fluid and medical treatment. When the pump mechanism 8 is to be operated, the program flow proceeds from step S10 to step S11 to operate the pump mechanism 8 by a key input. Then the pump mechanism 8 starts to deliver the fluid at the fluid delivery rate. When the pump mechanism 8 is in operation at step S2, the program flow proceeds to step S3. When it is detected by the pump mechanism rotation detector 10 that an incremental unit (1 ml in this case) has taken place, a value smaller by one than the current scheduled fluid volume is set up as a renewed scheduled fluid volume at step S4. When the power to the infusion apparatus is turned off by means of the power switch at step S5, the operation of the pump mechanism 8 is stopped at step S12 and the power is turned off to make the infusion apparatus enter into an off state to wait for the turning-on of the power at step S1. When it is determined at step S6 that the scheduled fluid volume has reduced to zero or when a request for stopping the operation of the pump mechanism 8 takes place due to a key input or the occurrence of an alarm, the program flow proceeds to step S7 to stop the operation of the pump mechanism 8. Then the program flow returns to step S2 to wait for an input of the next values of the fluid delivery rate and scheduled fluid volume.

The infusion apparatus requires periodical maintenance service a part of which requires service personnel to grasp the use condition of the infusion apparatus. For instance, there is the lead battery for backing up the AC power supply as an important component of the infusion apparatus. The lead battery gradually loses its charge capacity in the course of repeating charge and discharge operations which results in a reduced operable time and a need for replacement. Therefore, in order to determine the time for replacing the battery, the service personnel have recorded the total time of use of the infusion apparatus for the medical treatment to measure the degree of the deterioration of the charge capacity. However, on the same time of use basis, the power for charging the battery differs between the case where the battery has been used actually for operating the pump and the case where the infusion apparatus has been left unoperated while receiving a power. When the total time of use of the infusion apparatus includes the period of time in which the infusion apparatus is operated on the battery, the battery is not charged but discharged during the period of time. Therefore, it has been impossible to correctly measure the lifetime of the battery at all times only by the time of use of the infusion apparatus. In order to correctly perceive the lifetime of the battery, it is necessary to recognize the rate of the period of time in which the pump had actually operated and the rate of the period of time in which the power is supplied from the battery with respect to the total time in which the power is supplied to the infusion apparatus. Among the parts other than the lead battery, there are several parts requiring replacement after being used for a certain time. However, it is impossible for the service personnel who is neither a doctor nor a nurse to clock the time in the field where the infusion apparatus is used while referring to the use condition of the apparatus. It is also impossible for the doctor or nurse who is administering a medical treatment to clock the time. Meanwhile, it has been absolutely necessary to perceive the correct data in order to maintain the infusion apparatus serving as a therapeutic apparatus always in the best condition. As described above, the conventional infusion apparatus has been provided with an insufficient function in regard to the maintenance service for maintaining the quality of the infusion apparatus.

SUMMARY OF THE INVENTION

The object of the present invention is therefore to provide an infusion apparatus capable of informing the operator of the period of time in which a power is supplied from the AC power source or the battery, the actual operation time of the pump, and the period of time in which a power is supplied from the battery, separately.

In order to achieve the aforementioned object, there is an infusion apparatus which is operated on alternating current power source and includes a pump mechanism for transferring a fluid through an administration tube by repetitively pressing a portion of the administration tube in a peristaltic manner in a direction of transferring the fluid and a battery for backing up the alternating current power source, the infusion apparatus comprising: first clock means for clocking a period of time in which power is supplied to the infusion apparatus from the alternating current power source or the battery for backing up the alternating current power source; first storage means for storing the period of time clocked by the first clock means; second clock means for clocking a period of time in which power is supplied to the infusion apparatus from the battery; second storage means for storing the period of time clocked by the second clock means; third clock means for clocking a period of time in which the pump mechanism operates; third storage means for storing the period of time clocked by the third clock means; display means; and means for calling up the period of time stored in each of the first, second and third storage means to display the period of time on the display means.

By displaying the periods of time stored in the above-mentioned storage means in the above-mentioned arrangement, the total time in which power is supplied, the period of time in which power is supplied from the battery, and the operation time of the pump mechanism can be perceived. From the above-mentioned periods of time, the degree of degradation of the charge capacity of the battery and the times of use of the other parts can be perceived to allow the operator to easily recognize the times for replacing the battery and other parts.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The following describes the present invention with reference to embodiments as shown in the attached drawings.

Figure 1:
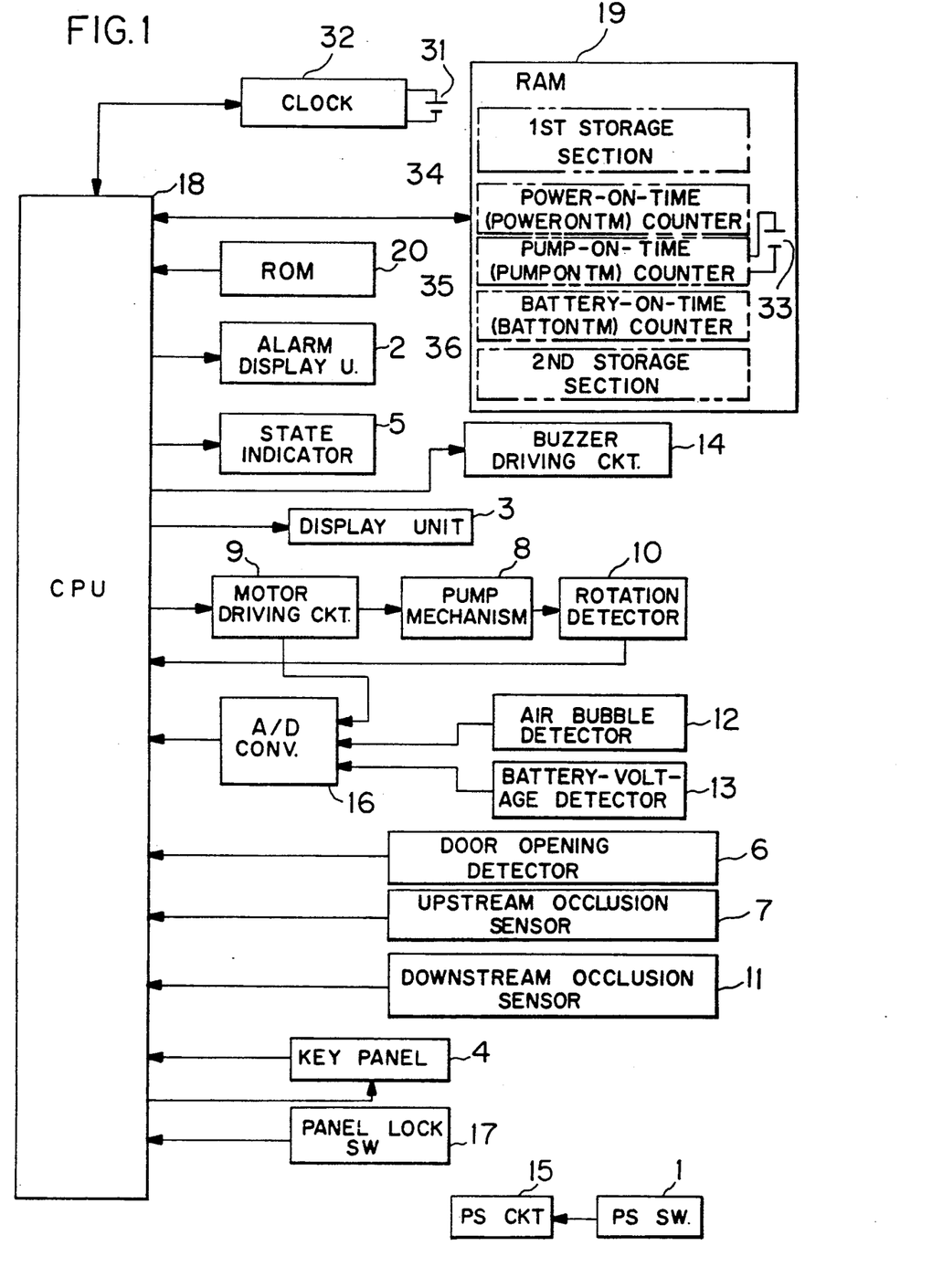
FIG. 1 is a block diagram of an embodiment of the present invention.

FIG. 1 is a block diagram of an embodiment of the present invention. The present infusion apparatus differs from the conventional infusion apparatus shown in FIG. 6 in that a clock unit 32 operating on a lithium battery 31 provided independently of the power source for the infusion apparatus is incorporated, a RAM (memory section) 19 includes three time counters, i.e., a power-on-time (Powerontm) counter 34 serving as first clock means and first storage means, a pump-on-time (Pumpontm) counter 35 serving as third clock means and third storage means, and a battery-on-time (Battontm) counter 36 serving as second clock means and second storage means, those three counters operating on a lithium battery 33 provided independently of the power source for the infusion apparatus, and the CPU 18 displays the count values of the counters 34, 35, and 36 on the display unit 3 in response to a request input from the key panel 4. The other portions are the same as those of the conventional infusion apparatus.

The Powerontm counter 34 is always incremental while the power to the infusion apparatus is on (while a power is supplied from the AC power line of the lead battery). The Pumpontm counter 35 is incremental only when the stepping motor of the pump mechanism 8 is in operation. The Battontm counter 36 is incremental while a power is supplied from the lead battery to the infusion apparatus. The above-mentioned three counters 34, 35, and 36 are each incremental every minute, i.e., unit time to store counter values in the form of "HRS MIN". Since the storage values of the counters 34, 35, and 36 are backed up by the lithium battery 33, the storage values are maintained even when the infusion apparatus is supplied with no power. The storage values are each displayed on the display unit 3 by the CPU 18 when a request for displaying the values from the key panel 4 has occurred.

Figure 2:
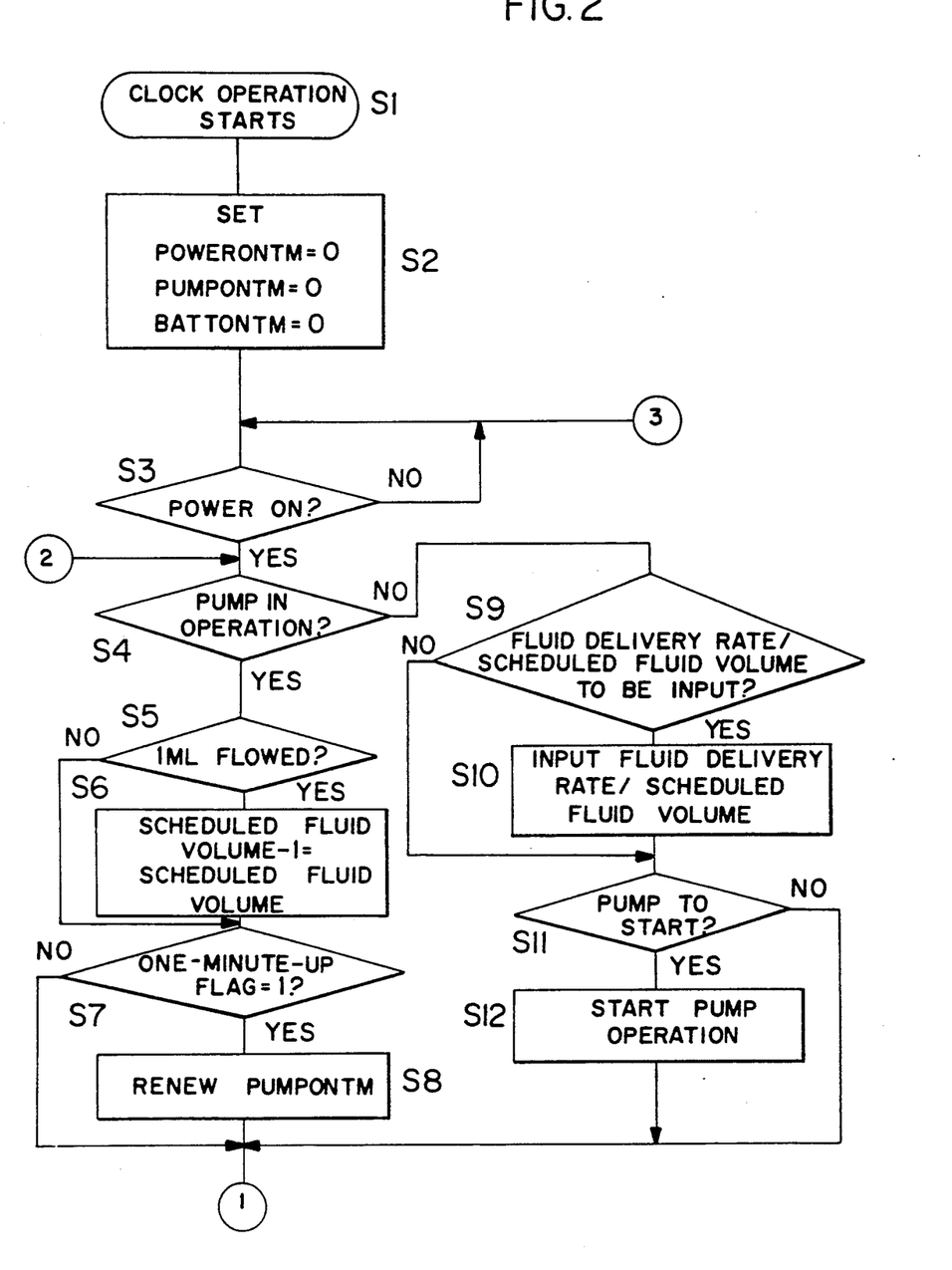
FIG. 2 is a flowchart of the operation of the embodiment shown in FIG. 1 to be continued to a flowchart as shown in FIG. 3.
Figure 3:
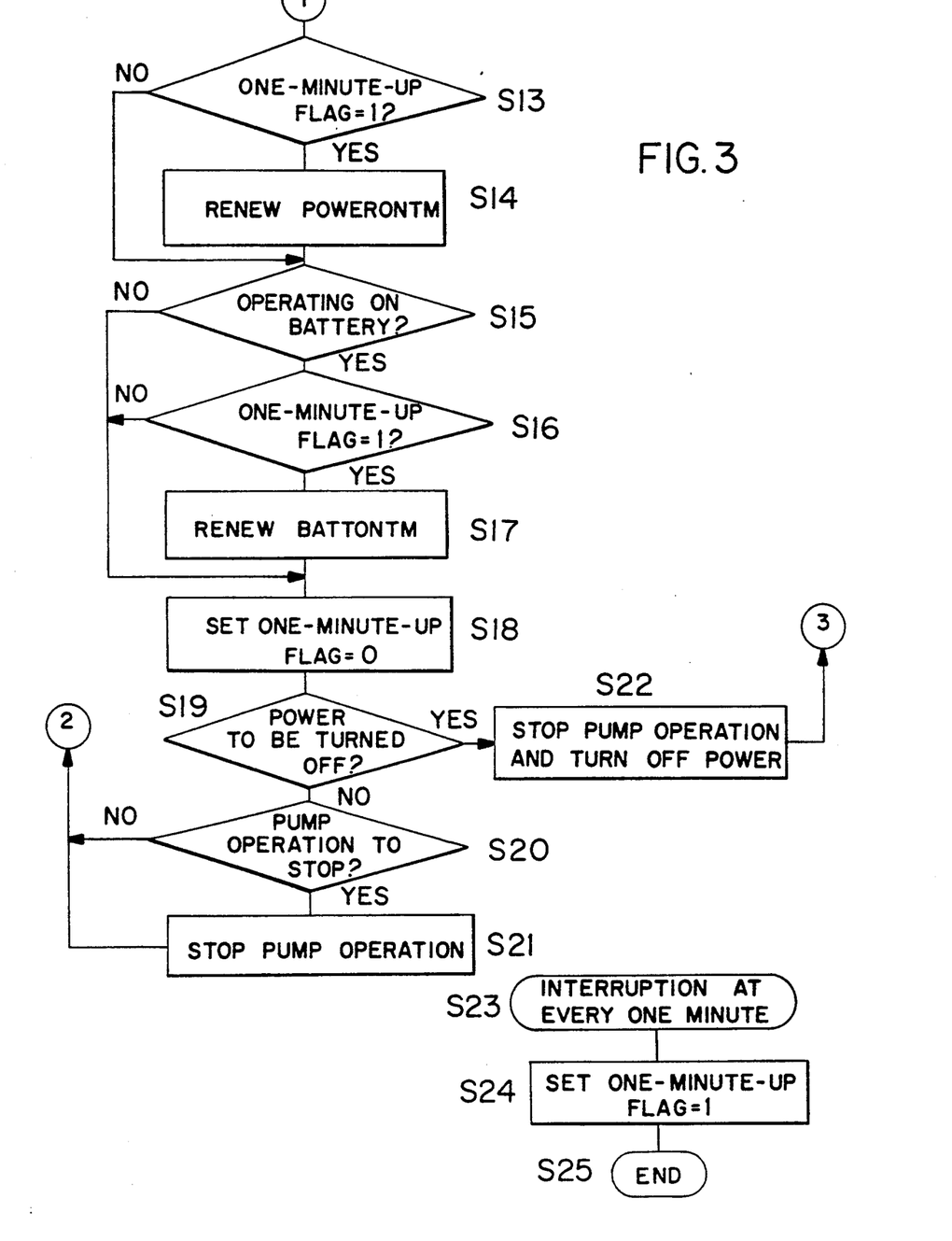
FIG. 3 is a flowchart continued from the flowchart shown in FIG. 2.

The following describes the operation of the present embodiment with reference to flowcharts as shown in FIGS. 2 and 3.

First, the clock unit 32 starts to operate at step S1. The above step is executed in the shipping stage of the infusion apparatus from the factory or at the time of resetting the clock in a special mode, however, the step is normally not executed whether the power of the infusion apparatus is turned on or off. Then an initial value of 0 is stored at step S2 in each of the Powerontm counter 34, Pumpontm counter 35, and Battontm counter 36 which are time counters backed up by the lithium battery 33. The operations of from step S1 to step S2 are executed in the shipping stage from the factory or at the time of resetting the clock, and not executed in the subsequent normal operation of the infusion apparatus. Since the clock unit 32 operates independently of the power to the infusion apparatus, it is possible to request an interruption to the work of the CPU 18. The CPU 18 can respond to the request for interruption by the clock unit 32 when the power is supplied. Since the present embodiment has its unit time of one minute, the clock unit 32 issues a request for interruption to the CPU 18 every time one minute has elapsed, and then the CPU 18 interrupts the normal processing and enters into an interruption subroutine from the step S23 (refer to FIG. 3). The interruption subroutine sets a one-minute-up flag to 1 at step S24 to allow the elapse of one minute to be recognized in the subsequent processes. Thereafter, the interruption subroutine ends, and the program flow returns to the normal process (step S25).

Then the normal process is explained. Because the time necessary for executing a loop per one normal process is shorter than one minute, the normal process is performed without any substantial disadvantage even if a delay due to the interruption occurs. When the power supply switch 1 starts to supply power to the infusion apparatus at step S3, it is determined at step S4 whether or not the pump mechanism 8 is in operation (i.e., is delivering fluid). When the pump mechanism 8 is not in operation, input of values of the fluid delivery rate and scheduled fluid volume can be performed. Therefore, when a request occurs, the program flow proceeds from step S9 to step S10 to allow input of values of the fluid delivery rate and scheduled fluid volume by means of key input or the like. When a request for starting the pump operation is issued at step S11, the pump mechanism 8 starts its operation at step S12 to start a fluid delivery. When it is determined that the pump is in operation at step S4, the program flow proceeds to step S5 to determine whether an incremental unit (1 ml in this case) has taken place based on a detection result from the pump mechanism rotation detector 10 as shown in FIG. 1. When an incremental unit of 1 ml has taken place, a value smaller by one than the current scheduled fluid volume is set up as a renewed scheduled fluid volume at step 26. When it is checked at step S7 whether or not the one-minute-up flag which is set by the interruption subroutine initiated by the clock unit 32 is already set. When the flag is already set, it can be found that one minute has elapsed. Only when the flag is set, the program flow proceeds to step S8 to increase by one the count value of the pump power-on-time (Pumpontm) counter 35. As is clear in the above description, there is an orientation for renewing the Pumpontm counter 35 at step S8 only when the pump mechanism 8 is in operation. When the pump mechanism 8 is not in operation, the program flow proceeds from step S9 through step S12 and then to step S13, and therefore the Pumpontm counter 35 is not incremented. Whether or not the pump mechanism 8 is in operation, the power is supplied so far as the power supply switch 1 is on. Therefore, when the one-minute-up flag is set up at 1, the power-on-time counter (Powerontm) 34 is renewed at step S13 and step S14. When the pump mechanism 8 is operating on the power from the battery, the battery-on-time counter (Battontm) 36 is incremented at step S15 through step S17 in the same manner as described above. After the three time counters 34, 35, and 36 are incremented by the one-minute-up flag, there is no counter to be incremented by the one-minute-up flag. Therefore, the one-minute-up flag is reset to 0 at step S18. In the above-mentioned process, the one-minute-up flag which was set after the elapse of one minute at step S23 through step S25 is reset after once increment each counter to be able to securely increment the counters after the elapse of one minute. The subsequent operation is the same as the conventional technique. When the power is turned off at step S19, after stopping the pump operation at step S22, the power is turned off. When the scheduled fluid volume is reduced to 0, or when a request for stopping the pump operation by the power supply switch 1 occurs, or when there is a need for immediately stopping the pump operation due to the occurrence of an alarm, the program flow proceeds to step S20 to step S21 to stop the pump operation to enter into the stop state.

FIGS. 4(a), 4(b), 4(c) and 4(d) show exemplified display patterns count values read out from of the time counters (34, 35 and 36). The display unit 3, which serves to display the count values, has three liquid crystal display lines of ten figures, where each figure is composed of 14 segments (refer to FIG. 4(a)). In the three-line display unit, the uppermost line displays the name of the counter currently on the display, the middle line displays a message (HRS MIN) for the discrimination between a hour value and a minute value, and the lowermost line displays the hour value and the minute value. For displaying the above messages, the infusion apparatus enters into a display mode and performs a switching between the following display items in the following order every time a call-up key is pressed (refer to FIGS. 4(b), 4(c), and 4(d)).

Figure 4A:
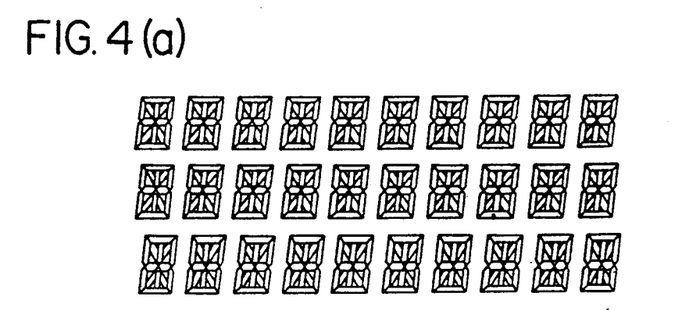
FIGS. 4(a), 4(b), 4(c) and 4(d) are views showing exemplified display patterns of the embodiment shown in FIG. 1.
Figure 4B:
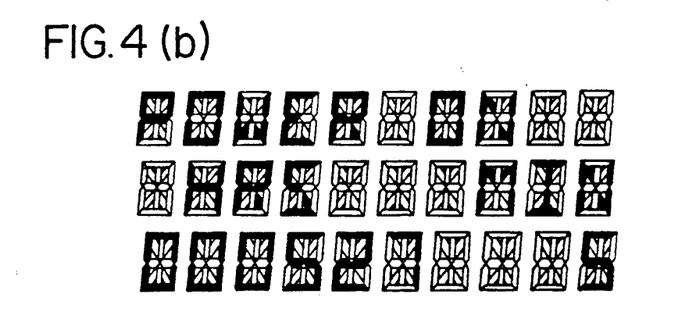
Figure 4C:
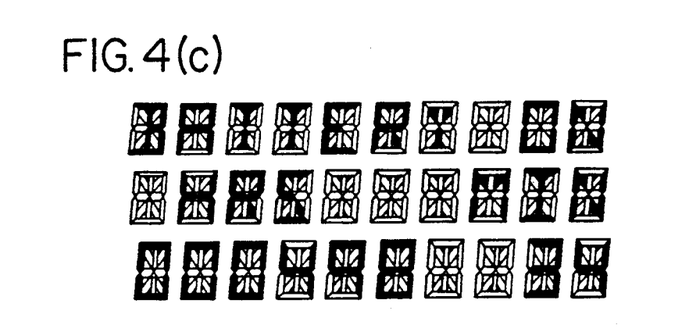
Figure 4D:
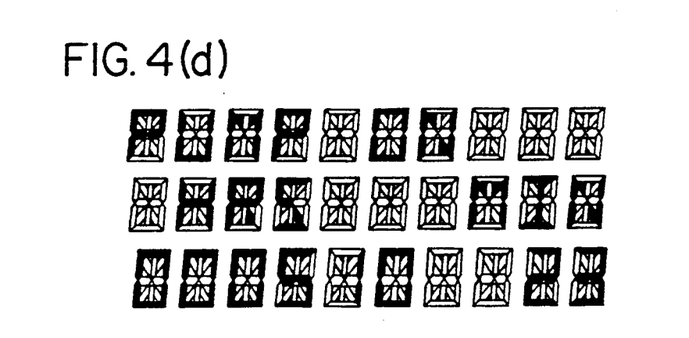

(1) Power-on-time display (Powerontm value display)
(2) Battery-on-time display (Battontm value display)
(3) Pump-on-time display (Pumpontm value display)

The message of the current counter name displayed on the uppermost line exhibits respectively (1) POWER ON, (2) BATTERY ON, and (3) PUMP ON. Since each counter data is stored with its hour value separated from its minute value, the hour value and the minute value are separately displayed on the lowermost hour/minute display line. The hour value is displayed by a six-figure number of 000000 to 999999, while the minute value is displayed by a two-figure number kf 00 to 59. The examples in FIGS. 4 (b), (c) and d) exhibit the fact that the power-on-time was 527 hours and 5 minutes, the battery-on-time was 498 hours and 34 minutes, and the pump-on-time was 510 hours and 23 minutes. The display items change in the order of FIG. 4 (b)→FIG. 4 (c)→FIG. 4 (d)→FIG. 4 (b)→FIG. 4 (c)→. . . .

As described above, the power-on-time counter 34, the pump-on-time counter 35, and the battery-on-time counter 36 are provided, and count values counted by them are displayed on the display unit 3. From the count values on display, the period of time in which a power is supplied to the infusion apparatus from the AC power source or the backup battery, the period of time in which a power is supplied to the infusion apparatus from the backup battery, and the period of time in which the pump mechanism 8 operates can be perceived. The above-mentioned time values indicate the degree of deterioration of the charge capability of the battery, from which the time of replacing the battery can be perceived. The above-mentioned time values also indicate the time of use of the other parts, from which the time for replacing each part can be perceived.

As described above, the present invention provides an infusion apparatus provided with first clock means for clocking a period of time in which power is supplied to the infusion apparatus from the AC power source or the battery for backing up the AC power source; first storage means for storing the period of time clocked by the first clock means; second clock means for clocking a period of time in which power is supplied to the infusion apparatus from the battery; second storage means for storing the period of time clocked by the second clock means; third clock means for clocking a period of time in which a pump mechanism operates; third storage means for storing the period of time clocked by the third clock means; display means; and means for calling up the period of time value stored in each of the first, second and third storage means to display the period of time on the display means. Therefore, by displaying the period of time stored in each of the first, second and third storage means on the display means at any time, the service personnel can perceive the time for replacing the battery and the other parts from the period of time to be able to recognize the appropriate time for servicing without resorting to any manual recording means.

The invention being thus described, it will be clear to one skilled in the art that the same may be varied in many ways. Such variations are not to be regarded as a departure from the spirit and scope of the invention, and all such modifications as would be clear to one skilled in the art are intended to be included within the scope of the following claims.

What is claimed is:

1. An infusion apparatus which is operated on alternating current power source and includes a pump mechanism for transferring a fluid through an administration tube by repetitively pressing a portion of the administration tube in a peristaltic manner in a direction of transferring the fluid and a battery for backing up the alternating current power source, the infusion apparatus comprising:
   first clock means for clocking a period of time in which power is supplied to the infusion apparatus from the alternating current power source or the battery for backing up the alternating current power source;
   first storage means for storing the period of time clocked by the first clock means;
   second clock means for clocking a period of time in which power is supplied to the infusion apparatus from the battery;
   second storage means for storing the period of time clocked by the second clock means;
   third clock means for clocking a period of time in which the pump mechanism operates;
   third storage means for storing the period of time clocked by the third clock means;
   display means; and
   means for calling up the period of time stored in each of the first, second and third storage means to display the period of time on the display means.

2. The infusion apparatus as claimed in claim 1, wherein the first clock means and the first storage means are constituted of a power-on-time counter; the second clock means and the second storage means are constituted of a battery-on-time counter; and the third clock means and the third storage means are constituted of a pump-on-time counter.

3. The infusion apparatus as claimed in claim 2, further including a random access memory, said random access memory including the power-on-time counter, the battery-on-time counter, and the pump-on-time counter.

4. The infusion apparatus as claimed in claim 3, further including a battery other than said battery for backing up the alternating current power source, said random access memory operating on said other battery.

* * * * *